United States Patent [19]

Kreutzberger et al.

[11] Patent Number: 5,712,407
[45] Date of Patent: Jan. 27, 1998

[54] METHOD FOR THE PREPARATION OF ALPHA-CHLORINATED CHLOROFORMATES

[75] Inventors: Charles B. Kreutzberger, Pittsburgh; Seetha Eswarakrishnan, Allison Park; Suresh B. Damle, Pittsburgh, all of Pa.

[73] Assignee: PPG Industries, Inc., Pittsburgh, Pa.

[21] Appl. No.: 782,991

[22] Filed: Jan. 14, 1997

[51] Int. Cl.$^6$ ............................ C07C 68/02; C07C 69/96
[52] U.S. Cl. .......................... 558/283; 558/282; 502/167; 502/162; 549/499
[58] Field of Search ........................ 558/283, 282; 502/167, 162; 549/499

[56] References Cited

U.S. PATENT DOCUMENTS

| | | | |
|---|---|---|---|
| 4,592,872 | 6/1986 | Cagnon | 558/281 |
| 4,592,874 | 6/1986 | Cagnon | 558/283 |
| 4,614,829 | 9/1986 | Malfroot | 558/283 |
| 4,806,286 | 2/1989 | Senet | |
| 5,298,646 | 3/1994 | Guzik et al. | 558/283 |
| 5,616,771 | 4/1997 | Kahl | 558/282 |

FOREIGN PATENT DOCUMENTS 160740  10/1973  Hungary.

*Primary Examiner*—C. Warren Ivy
*Assistant Examiner*—Jean F. Vollano
*Attorney, Agent, or Firm*—Irwin M. Stein

[57] ABSTRACT

Novel catalysts for the synthesis of a alpha-chlorinated chloroformate from an aldehyde and phosgene are described. The catalysts include alkyl substituted guanidines, hexasubstituted guanidinium chlorides, substituted biguanidinium chloride, phenyldialkyliminiumtetraalkylguanidinium chloride, dialkylimidazolinium tetraalkylguanidinium chloride, phenyltetraalkylamidinium chloride and N,N-dialkyl-N'-alkylpyrrolidinium chloride.

12 Claims, No Drawings

METHOD FOR THE PREPARATION OF ALPHA-CHLORINATED CHLOROFORMATES

FIELD OF THE INVENTION

The invention relates to catalysts for the synthesis of alpha-chlorinated chloroformates.

BACKGROUND OF THE INVENTION

A number of specialty chemicals are produced using alpha-chlorinated chloroformares as starting materials. In particular, 1-chloroalkyl chloroformates are used as starting materials to prepare carbonate derivatives that are used in the pharmaceutical industry.

The synthesis of alpha-chlorinated chloroformares having the formula,

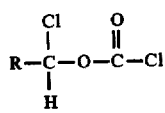

(I)

wherein R is an aliphatic, aromatic or heterocyclic group, has been a difficult undertaking if it is essential not to add further chlorine to the R group during the synthesis. In Liebig's Annalen der Chemie of 1890, Volume 257, page 50 et seq., a process is described for photolyrically chlorinating the corresponding chloroformate which is unsubstituted in the alpha-position. Unfortunately, numerous by-products which are more highly chlorinated than desired and isomers are obtained in addition to the desired product. These by-products are difficult to separate from the desired product.

The synthesis of alpha-chlorinated chloroformares by reacting a trichloromethyl derivative chosen from trichloromethyl chloroformate and di(trichloromethyl) carbonate with an aldehyde in a particular reaction medium and in the presence of a compound such as pyridine, alkylpyridines, amides that are disubstituted on the nitrogen, ureas, tetrasubstituted thioureas, and phosphoroamides substituted on the nitrogen is described in U.S. Pat. No. 4,614,829.

The synthesis of alpha-chlorinated chloroformares by the reaction of an aldehyde with phosgene in the presence of a catalyst has been described in U.S. Pat. Nos. 4,592,872 and 4,592,874. The catalysts described in the '872 patent are pyridine, N,N-dimethylaminopyridine, imidazole, tertiary aliphatic phosphines, and amides, ureas, thioureas and phosphoramides wherein the nitrogen atoms are completely substituted by alkyl groups. The '874 patent describes catalysts selected from (a) quaternary ammonium, phosphonium or arsonium halogenide having hydrocarbyl radicals attached to the Nitrogen, Phosphorous or Arsenic atom which hydrocarbyl radicals have together at least 15 carbon atoms, and (b) metal halogenides associated with a crown ether or a cryptand.

Guanidine derivatives, in particular hexasubstituted guanidine derivatives, have been used as catalysts in the preparation of carboxylic acid chlorides. U.S. Pat. No. 4,806,286 describes phosgenation of carboxylic acids in the presence of hexasubstituted guanidinium salts or their complexes with organic acids. In the reaction, phosgene reacts with a carboxylic acid in the presence of the catalyst to produce the corresponding carboxylic acid chloride, hydrogen chloride (HCl) and carbon dioxide ($CO_2$). The carbon atom of the phosgene reactant does not become incorporated in the carboxylic acid chloride; but, instead is released as $CO_2$. In contrast, during the synthesis of 1-chloroalkyl chloroformares by the reaction of an aldehyde with phosgene, the phosgene reactant becomes part of the 1-chloroalkyl chloroformate.

It has now been discovered that guanidine derivatives catalyze the incorporation of phosgene into an aldehyde to produce alpha-chlorinated chloroformates.

SUMMARY OF THE INVENTION

In accordance with the present invention, alpha-chlorinated chloroformates of graphic formula (I)

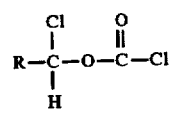

(I)

wherein R is selected from the group consisting of hydrogen, a substituted or unsubstituted aliphatic group, a substituted or unsubstituted aromatic group, or an alicyclic or heterocyclic group are synthesized by reacting phosgene with an aldehyde of the general formula RCHO (as hereinafter defined) in the presence of a catalyst selected from the group consisting of compounds of graphic formulae II–VIII.

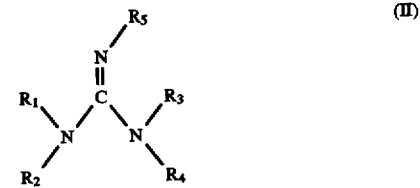

(II)

(III)

(IV)

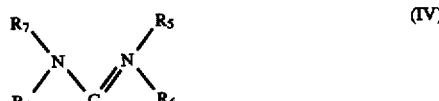

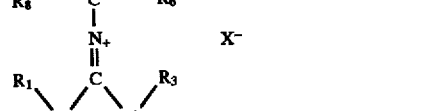

(V)

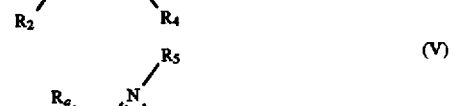

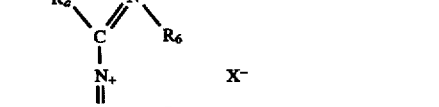

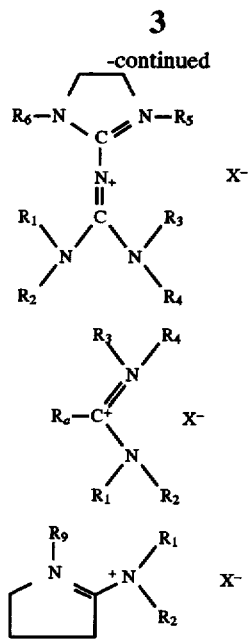

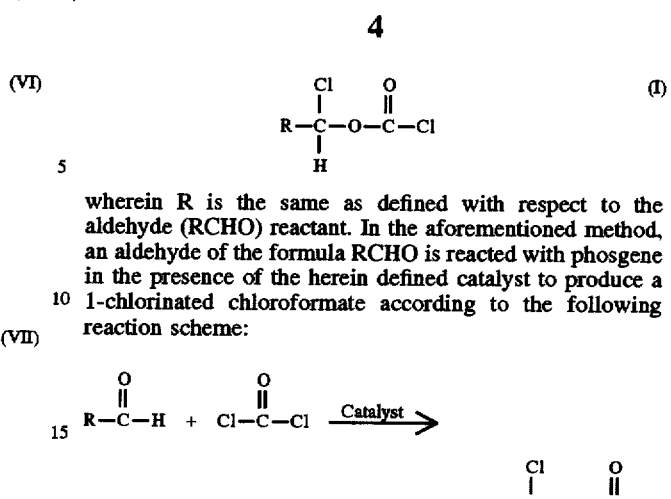

wherein R is the same as defined with respect to the aldehyde (RCHO) reactant. In the aforementioned method, an aldehyde of the formula RCHO is reacted with phosgene in the presence of the herein defined catalyst to produce a 1-chlorinated chloroformate according to the following reaction scheme:

$$R-\overset{O}{\overset{\|}{C}}-H + Cl-\overset{O}{\overset{\|}{C}}-Cl \xrightarrow{\text{Catalyst}}$$

$$R-\overset{Cl}{\underset{|}{C}H}-O-\overset{O}{\overset{\|}{C}}-Cl$$

By the term "catalyst", it is meant to include a material which does not participate in the reaction and is used in relatively small amounts compared to the principal reactants, i.e., the aldehyde and phosgene. The catalyst of the present invention may be separated and recovered from the end product by methods known to those of ordinary skill in the art and reused in a subsequent reaction between phosgene and an aldehyde.

The catalysts of the present invention include compounds represented by graphic formulae II–VIII, as detailed hereinabove, wherein X is chloro or bromo, preferably chloro, and $R_1$, $R_2$, $R_3$, $R_4$, $R_5$, $R_6$, $R_7$ and $R_8$ are the same or different and each are hydrogen or a $C_1$–$C_8$ alkyl, preferably a $C_1$–$C_4$ alkyl, and $R_9$ is a $C_1$–$C_{12}$, e.g., $C_1$–$C_4$, alkyl group. $R_a$ is phenyl, monosubstituted phenyl, or $C_1$–$C_{20}$, e.g., $C_1$–$C_{10}$, or $C_1$–$C_4$, alkyl. The phenyl substituents may be $C_1$–$C_4$ alkyl or halogen, e.g., fluorine, chlorine or bromine, preferably chlorine. Suitable catalysts include tetrasubstituted guanidine, e.g., tetraalkylguanidine such as tetrabutyl guanidine, pentasubstituted guanidine, e.g., pentaalkyl guanidine such as pentabutyl guanidine, hexasubstituted guanidinium chloride or bromide, e.g., hexaalkyl guanidinium chloride or bromide such as hexaethyl guanidinium chloride and hexabutylguanidinium chloride, substituted biguanidinium chloride or bromide, e.g., octaalkyl biguanidinium chloride or bromide such as octamethyl biguanidinium chloride, and octabutyl biguanidinium chloride, phenyldialkyliminiumtetraalkylguanidinium chloride or bromide, such as phenyldiethyliminiumtetramethylguanidinium chloride, dialkylimidazoliniumtetraalkylguanidinium chloride or bromide, such as dimethylimidazoliniumtetrabutylguanidinium chloride, phenyltetraalkylamidinium chloride or bromide, such as phenyltetraethylamidinium chloride, N,N-dialkyl-N'-alkylpyrrolidinium chloride or bromide, such as N,N-dibutyl-N'-octylpyrrolidinium chloride and bromide, and their corresponding hydrochloride or hydrobromide salts. A preferred catalyst is pentabutylguanidine, a member of the catalyst group of graphic formula II wherein $R_1$, $R_2$, $R_3$, $R_4$ and $R_5$ are all butyl groups, and its hydrochloride salt.

The particular R groups of the catalysts ($R_1$–$R_9$) are controlled by the source of the starting materials. Commercially available starting materials, such as tetrasubstituted urea, are symmetrical, that is, $R_1$, $R_2$, $R_3$ and $R_4$ are all the same. Syntheses of the catalysts of the present invention are described hereinafter.

Aldehydes that may be used in the herein-described method of producing 1-chlorinated chloroformates include The aforedescribed catalyst is present in catalytic amounts, i.e., in amounts sufficient to catalyze the reaction of an aldehyde of the formula RCHO (as defined herein) with phosgene. More particularly, the catalyst is used in amounts of from 0.001 to 10 mole %, based on the molar amount of aldehyde used, preferably from 0.5 to 5 mole % based on the molar amount of aldehyde used.

At least a stoichiometric amount of phosgene is used in the synthesis reaction. The reaction preferably takes place with an excess of phosgene. Generally, the mole ratio of phosgene to aldehyde is from 1.1–1.2 moles of phosgene to 1 mole of aldehyde. However, a larger excess of phosgene may be used, if desired.

The aldehyde (RCHO) used to prepare the alpha-chlorinated chloroformares are aldehydes that may be selected from those wherein R is a substituted or unsubstituted $C_1$–$C_{20}$ aliphatic group, e.g., $C_1$–$C_{20}$ alkyl or $C_2$–$C_{20}$ monoethylenically unsaturated olefin, more typically $C_1$–$C_{12}$ alkyl or $C_2$–$C_{12}$ monoolefin, more particularly $C_1$–$C_4$ alkyl such as methyl, ethyl, propyl and butyl, or $C_2$–$C_4$ olefin; substituted or unsubstituted aromatic group, e.g., phenyl; and alicyclic and heterocyclic groups such as cyclohexyl and 2-furyl. The substituents for the aliphatic aldehydes can be halogen, e.g., fluorine, chlorine and bromine, cyano and nitro. The aromatic substituents can be $C_1$–$C_4$ alkyl groups and halogen, e.g., fluorine chlorine and bromine. The aliphatic and aromatic halogen substituent is preferably chlorine, and the aliphatic group can be branched or straight chain.

DETAILED DESCRIPTION OF THE INVENTION

As used in this description, examples and claim, all percentages, ratios and parts are by weight, unless otherwise specifically indicated; and other than in the operating examples, or where otherwise indicated, all numbers expressing quantities of components or reaction conditions used herein are to be understood as modified in all instances by the term "about".

The present invention is directed to a method of synthesizing alpha-chlorinated chloroformares of the following graphic formula I:

the heretofore described aliphatic aldehydes, aromatic aldehydes, alicyclic aldehydes and heterocyclic aldehydes and dialdehydes. Examples of saturated aliphatic aldehydes include: acetaldehyde (ethanal), propanal, butanal, isobutanal, pentanal, hexanal, and chloromalonaldehyde. A suitable unsubstituted olefinic aldehyde is acrylaldehyde (acrolein). A suitable substituted aliphatic aldehyde is trichloroethanal (chloral). Suitable aromatic aldehydes include benzaldehyde, terephthaldehyde, substituted benzaldehydes (such as halo-substituted benzaldehyde, e.g., chlorobenzaldehyde) and $C_1$–$C_4$ alkyl substituted aromatic aldehydes, such as methylated benzaldehyde. A suitable aliyclic aldehyde is cyclohexanecarbaldehyde. A heterocyclic aldehyde that can be used is 2-furaldehyde (furfural).

The reaction mixture contains at least a stoichiometric mole ratio of phosgene to aldehyde. Preferably, the mole ratio of phosgene to aldehyde is from 1.1–1.2 to 1 in order to drive the reaction to form the chlorinated chloroformate. A larger excess of phosgene may be used but is not required and may not be economically attractive unless it can be recovered and used again. In practice, the phosgene is preferably added to a reaction chamber containing a premix of the aldehyde and the catalyst.

The reaction may take place in a solvent, preferably an aprotic solvent, to prevent the formation of hydrochloric acid. Suitable solvents that may be used include carbon tetrachloride, chloroform, methylene chloride, acetonitrile and aromatic solvents, such as toluene.

Phosgene is added typically to the premix of aldehyde and catalyst at a temperature of from 0° to 70° C., preferably from 0° to 30° C., and more preferably from room temperature (about 22° C.) to 30° C. If charged as a gas, the phosgene canbe sparged into the reaction mixture from a sparger located below the liquid surface of the reaction medium. Lower temperatures prevent the reversion of the 1-chlorinated chloroformate end product to the starting materials. While the phosgene reactant is commonly added to the aldehyde-catalyst-solvent premix, it is possible to reverse the order of addition, i.e., add the premix to a pool of phosgene.

The reaction is preferably performed in a glass-lined vessel at atmospheric pressure. The reaction vessel may be pressurized up to 10 pounds per square inch (psi) (68 kPa) if the reaction is relatively slow. The amount of catalyst used may be increased or decreased to speed up or slow down the reaction time, respectively. Because phosgene and some aldehydes, e.g., acetaldehyde, typically are gases at room temperature, the reaction vessel includes a reflux condenser.

Phosgene is usually charged, e.g. metered, into a premix of the aldehyde reactant and catalyst, which is typically present in the premix at a concentration of 1 mole %, based on the number of moles of aldehyde reactant used, and the reaction allowed to proceed. The phosgene can be charged to the premix at a rate appropriate for the rate of the reaction, i.e., the faster the reaction, the faster the rate at which phosgene can be charged to the reactor, and vice-versa. Once the reaction is complete, the reaction vessel is degassed to remove excess phosgene, which is neutralized by passing it through a caustic scrubber. The overall duration of the reaction is not critical and will depend on the catalyst level, the reactivity of the aldehyde and the temperature of the premix. Typically, at a catalyst concentration of 1 mole percent in the premix, the reaction period will be about 8 hours at temperatures of from room temperature to 30° C.

Ideally, at the end of the reaction no aldehyde reactant remains and the reaction vessel contains only catalyst and the 1-chlorinated chloroformate product after degassing.

The contents of the reaction vessel are distilled at moderate temperatures and at a reduced pressure, e.g., 28 inches of mercury (Hg) (95 kPA) to avoid reversion of the 1-chlorinated chloroformate product to the starting materials. Certain by-products including aldehyde trimers and aldehyde dimers may be present in the end product mixture and are separated during distillation. For the product prepared from acetaldehyde and phosgene, distillation temperatures are typically from 45° C. to 55° C.

Following distillation of the 1-chlorinated chloroformate, the bottoms remaining in the distillation column contain the catalyst, which may be rich in the 1-chlorinated chloroformate. The catalyst alone or catalyst rich in 1-chlorinated chloroformate may be reused in a subsequent reaction to produce additional 1-chlorinated chloroformate. Yields of at least about 90% based on the starting aldehyde reactant have been obtained from the use of the catalysts of the present invention.

Typically, it is contemplated that the reaction will be performed as a batch process in an appropriate reactor, and that distillation of the reaction product will be performed using the reactor as the distillation pot. The alpha chlorinated chloroformares are recovered by degassing the reactor and product to remove phosgene, and distilling the product at reduced pressures to separate the product from by-products, e.g., dimers and timers, and catalyst. For an aldehyde like acetaldehyde, distillation pressures of 27–28 inches of mercury (91–95 kPa) and distillation pot temperatures of 45° C. to 55° C., e.g., 47°–49° C., may be used.

The catalysts of the present invention, particularly the guanidine derivatives of graphic formulae II–V, may be prepared by reacting a tetraalkyl urea with phosgene to yield a chloroformamidinium chloride intermediate compound, which is subsequently condensed with ammonia or a primary amine to yield the corresponding guanidine derivative. The guanidine derivative may react further with the intermediate chloroformamidinium compound to produce a biguanidine derivative, such as that depicted in graphic formulae IV and V.

The synthesis reaction for the tetraalkyl- or pentaalkylguanidine catalyst of graphic formula II, such as pentabutylguanidine, may be as follows:

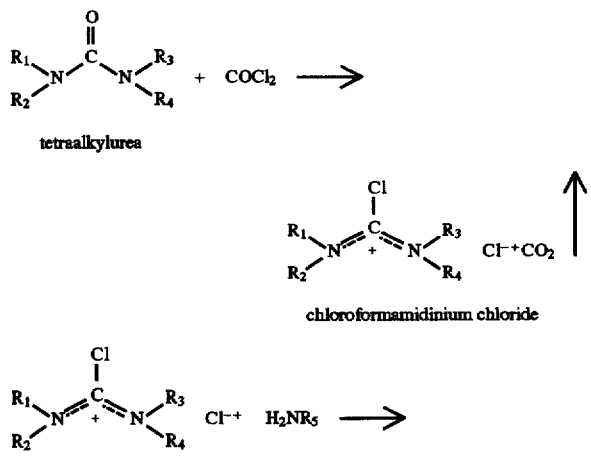

-continued

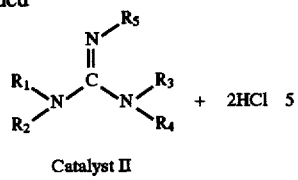

Catalyst II wherein $R_1$–$R_5$ are heretofore defined. The $H_2NR_5$ compound in the aforedescribed reaction sequence is used in amounts sufficient to form the $R_5$ group on the catalyst and, if desired, to serve as a hydrogen chloride acceptor for the hydrogen chloride liberated from the intermediate compound. Alternatively, some other base that is a hydrogen chloride acceptor, e.g., tertiary amine, can be used as a hydrogen chloride acceptor. The synthesis of pentaalkylguanidines is also described in Barcelo et al., Pentaalkylguanidines as Etherification and Esterification Catalysts, *Tetrahedron*, Vol. 46, No. 6, pp. 1839–1848 (1990); Barton et al., Synthesis and Properties of a Series of Sterically Hindered Guanidine Bases, *J. Chem. Soc. Perkin Trans. I*, pp. 2085–2090 (1982); and U.S. Pat. No. 5,082,968.

Hexaalkylguanidium catalysts that are depicted in graphic formula III may be synthesized by the reaction illustrated in the following equations:

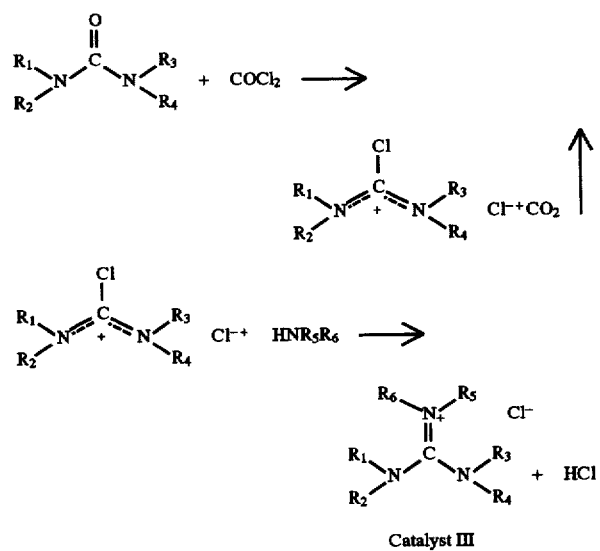

Catalyst III

A sufficient amount of the $HNR_5R_6$ reactant, Catalyst III or other base is used to scavenge the hydrogen chloride liberated in the synthesis. The synthesis of hexaalkylguanidium salts has also been disclosed in U.S. Pat. Nos. 5,082,468 and 4,806,286.

The octaalkylbiguanidinium chloride catalysts of graphic formula IV, such as tetrabutyltetramethylbiguanidinium chloride, may be synthesized by the reaction illustrated in the following equations:

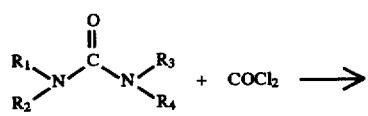

-continued

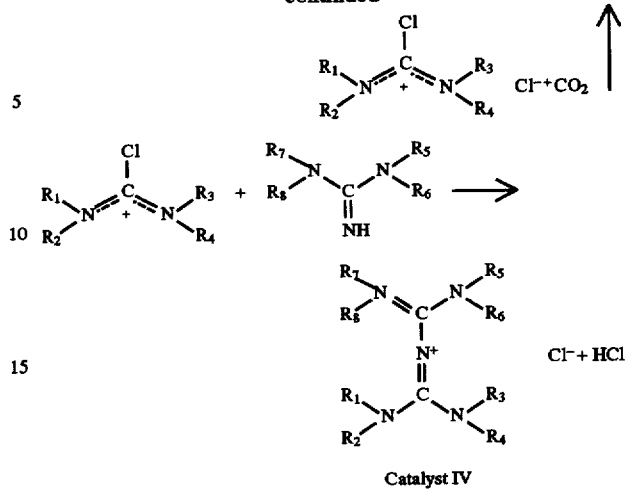

Catalyst IV

The reaction of the tetraalkylamidinium chloride with tetraalkylguanidine preferably takes place in acetonitrile. The synthesis can also be performed using a tertiary amine instead of a tetraalkylguanidine as the hydrogen chloride acceptor.

The phenyltetraalkylamidinium chloride catalysts depicted in graphic formula VII may be synthesized by the reaction sequence illustrated in the following equations:

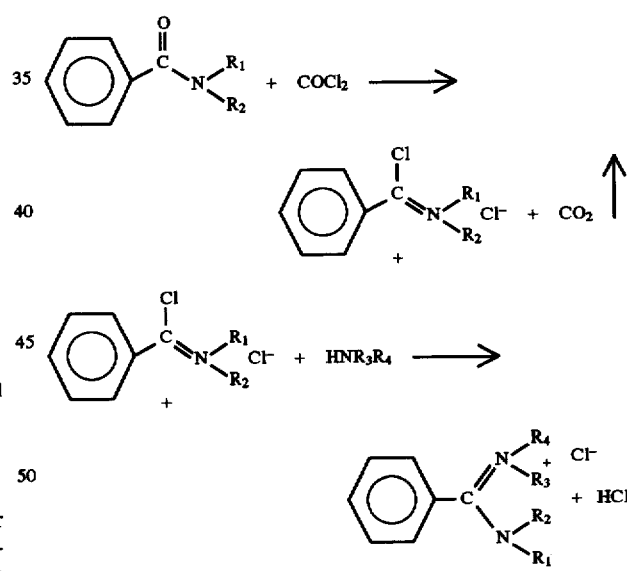

The phenyldialkyliminiumtetraalkylguanidinium chloride catalyst of graphic formula V, such as phenyldiethyliminiumtetramethylguanidinium chloride, may be synthesized by the reaction sequence illustrated in the following equations:

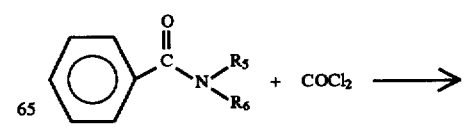

-continued

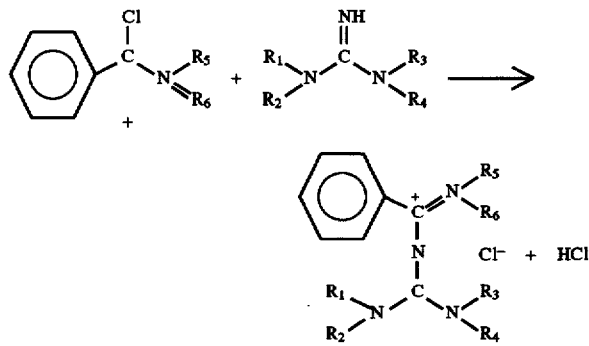

The reaction of the dialkylbenziminium chloride with tetraalkylguanidine preferably takes place in chloroform.

The dialkylimidazoliniumtetraalkylguanidinium chloride catalysts depicted in graphic formula VI may be synthesized by the reaction sequence illustrated in the following equations:

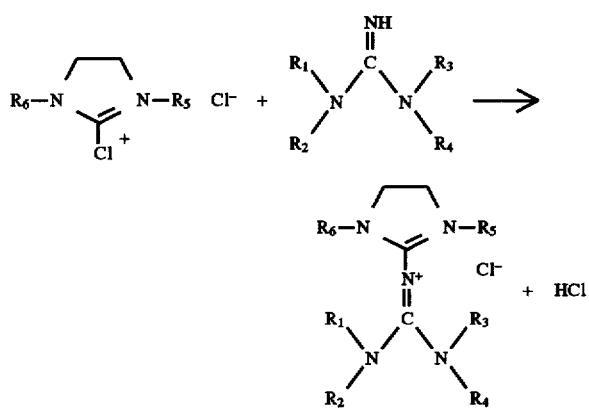

The imidazolinium chlorides are commercially available. The reaction preferably takes place in acetonitrile.

The N,N-dialkyl-N'-alkylpyrrolidinium chloride catalysts depicted in graphic formula VIII may be synthesized by the reaction sequence illustrated in the following equations:

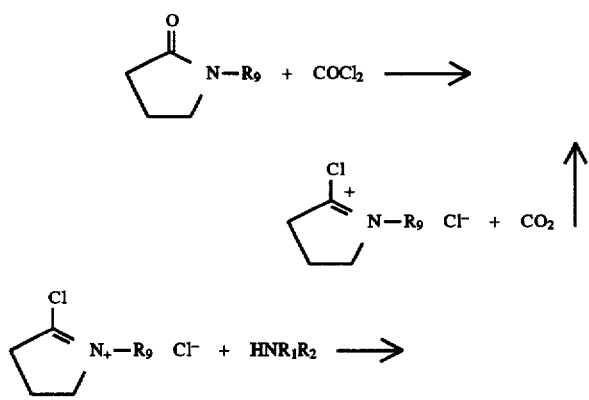

-continued

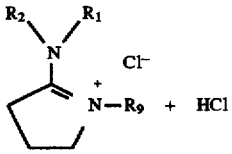

Although the invention has been described generally above, particular examples give additional illustration of the catalysts and method steps typical of the present method of synthesizing alpha-chlorinated chloroformares.

EXAMPLE 1

Synthesis of Tetrabutyltetramethylbiguanidium Chloride

To a cooled solution (0° C.) of 5.75 grams (g) (0.017 mol) of tetrabutylamidinium chloride in 20 milliliters (ml) of HPLC acetonitrile, 3.90 g (0.034 mol) of tetramethylguanidine was added via a syringe over five minutes. A white solid formed and the mixture was warmed to room temperature and allowed to stand for one hour. A solvent of 20 ml of diethyl ether was added and the solid precipitate was separated by filtration. The filtrate was concentrated at reduced pressure to an amber oil. The product was analyzed using nuclear magnetic resonance (NMR) analytical methods. Reported results of the analysis were as follows: $^1$H NMR (CDCl$_3$) δ3.18–2.87 (m, 8 H), 3.06 (s, 12 H), 1.61–1.46 (m, 8 H), 1.39–1.27 (m, 8 H), 0.96 (t, 12 H); $^{13}$C NMR (CDCl$_3$) δ164.6 (C=N), 51.2 (–CH$_2$N), 40.5 (CH$_3$N—), 29.7 (—CH$_2$—), 20.2 (—CH$_2$), 13.8 (CH$_3$—).

EXAMPLE 2

Synthesis of N,N-dimethylimidazoliniumtetramethyl Guanidine

To a room temperature solution of 5.52 g (0.033 mol) N,N-dimethylimidazolinium chloride in 20 ml of HPLC grade acetonitrile, 7.52 g tetramethylguanidine (0.065 mol) was added via a syringe over five minutes. The mixture was stirred for one hour. Tetramethylguanidinium hydrochloride salts were separated by filtration. The filtrate was concentrated in vacuo to give 6.83 g of a solid yellow product. NMR analysis reported the following results. $^1$H NMR (CDCl$_3$) δ3.84 (s, 4 H), 3.01 (s, 12 H), 2.89 (s, 6 H).

EXAMPLE 3

Synthesis of N,N-diethylphenyliminiumtetramethylguanidine

To a cooled solution (–78° C.) of 2.58 g (0.011 mol) diethylbenziminium chloride (the reaction product of diethylbenzamide and phosgene) in chloroform, 2.60 g (0.022 mol) of tetramethylguanidine was added over five minutes. The reaction mixture was allowed to warm to room temperature and stand for one hour. The reaction mixture was concentrated at reduced pressure and then diluted with a mixture of acetone and diethyl ether. The tetramethylguanidinium hydrochloride salt was separated by filtration. The filtrate was concentrated at reduced pressure to a glassy gum which solidified upon standing. The crystalline product was analyzed by NMR and the reported results were the following: $^1$H NMR (CDCl$_3$) δ7.61—7.58 (m, 3 H), 7.31–7.29 (m, 2 H), 3.75 (q, 2 H), 3.39 (q, 2 H), 2.87 (s, 12 H), 1.37 (t, 3 H), 1.23 (t, 3 H); $^{13}$C NMR (CDCl$_3$) δ166.6, 166.3, 132.4, 131.6, 129.8, 126.1, 45.8, 43.5, 41.1, 14.3, 12.5.

EXAMPLE 4

Synthesis of 1-chloroalkylchloroformate

A jacketed 1 liter four-necked kettle top reactor was fitted with a thermocouple, acetaldehyde inlet, a mechanical stirrer with a TEFLON® polytetrafluoroethylene coated multi-paddle agitator and a coil condenser. Both the reactor and coil condenser were cooled by a circulating bath set at −10° to −15° C. Acetaldehyde (165.0 grams) (210 ml, 3.74 mol) was charged into the cooled reactor.

The acetaldehyde was maintained at 0° to 5° C. and the acetaldehyde inlet was replaced with a phosgene inlet. Pentabutylguanidine (12.7 g, 0.037 mol) catalyst was added to the reactor. Phosgene (458.7 g, 4.64 mol) was subsequently added to the reactor at a rate of 1 g/min over eight hours while maintaining the reaction mixture at a temperature of 5° to 10° C. with external cooling. Aliquots of the reaction mixture removed from the reactor after phosgene addition showed the reaction to be about 90% complete. Cooling of the reactor was discontinued and the mixture was allowed to equilibrate to room temperature, i.e., about 24° C. Stirring at room temperature was continued for twelve hours until no acetaldehyde could be detected by infrared analysis. The acetaldehyde carbonyl stretch at 1729 cm$^{-1}$ and the chloroformate absorbance at 1783 cm$^{-1}$ was monitored.

The reaction mixture was then degassed at 5 to 25 inches Hg (16.9–84.6 kPa) through a coiled condenser kept at −10° C. The phosgene was stripped by venting to a caustic bubble trap through a diaphragm pump and then venting to a main caustic scrubber.

Following degassing, the coil condenser was removed and replaced with a short path distillation head. The condenser for the distillation was kept at −10° C. and the distillation flask was held at 0° C. in an ice bath. Distillation at 47° to 49° C. and 27.5 to 28 inches Hg (93 to 95 kPa) produced 475.6 g of 1-chloroethylchloroformate or a yield of 88.9%. A gas chromatographic assay confirmed that the product was at least 99% 1-chloroethylchloroformate. The residue (39.9 g) in the reactor included pentabutylguanidine catalyst and 1-chloroethylchloroformate.

Although the invention has been described with particularity in the above text and examples, the invention is only to be limited insofar as is set forth in the accompanying claims.

What is claimed is:

1. In the method of synthesizing alpha-chlorinated chloroformate by the reaction of phosgene with an aldehyde in the presence of a catalyst, the improvement wherein the catalyst is selected from the group consisting of: tetrasubstituted guanidine, pentasubstituted guanidine, hexasubstituted guanidinium halide, substituted biguanidinium halide, phenyldialkyliminiumtetraalkylguanidinium halide, dialkylimidazoliniumtetraalkylguanidinium halide, phenyltetraalkylamidinium halide, N,N-dialkyl-N'-alkylpyrrolidinium halide and the hydrochloride or hydrobromide salts of such catalysts, the halide of such catalysts being the chloride or bromide.

2. The method of claim 1 wherein the catalyst is represented by a general formula selected from the group consisting of:

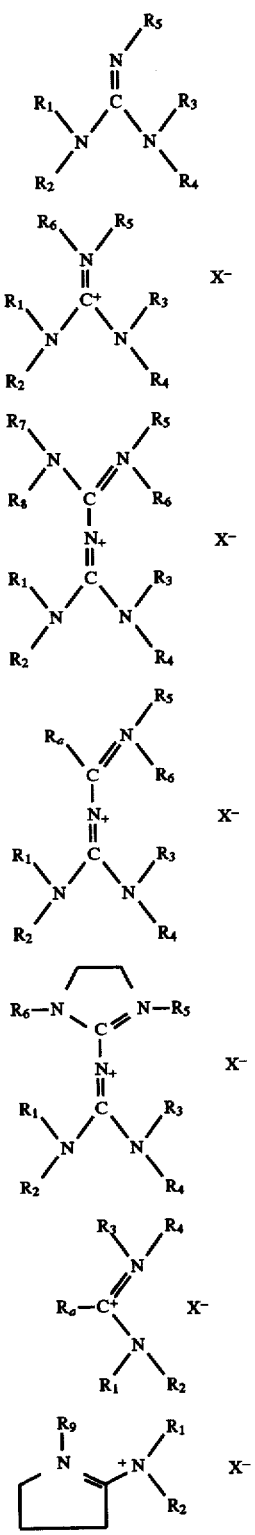

wherein X is chloro or bromo, $R_1$, $R_2$, $R_3$, $R_4$, $R_5$, $R_6$, $R_7$ and $R_8$ are each selected from the group consisting of hydrogen and $C_1$–$C_8$ alkyl, $R_9$ is a $C_1$–$C_{12}$ alkyl, and $R_a$ is phenyl, monosubstituted phenyl or $C_1$–$C_{20}$ alkyl, the phenyl substituent being selected from $C_1$–$C_4$ alkyl, fluorine, chlorine or bromine.

3. The method of claim 2 wherein X is chloro, $R_1$, $R_2$, $R_3$, $R_4$, $R_5$, $R_6$, $R_7$ and $R_8$ are each selected from the group consisting of hydrogen and $C_1$–$C_4$ alkyl, $R_9$ is a $C_1$–$C_4$ alkyl, and $R_a$ is phenyl, monosubstituted phenyl or $C_1$–$C_4$ alkyl, the phenyl substituent being selected from $C_1$–$C_4$ alkyl and chlorine.

4. The method of claim 2 wherein the aldehyde is represented by the formula RCHO, wherein R is a substituted or unsubstituted $C_1$–$C_{20}$ aliphatic group, a substituted or unsubstituted aromatic group, an alicyclic group and a heterocyclic group, the aliphatic substituents being halogen, cyano or nitro, and said aromatic substituents being halogen or $C_1$–$C_4$ alkyl.

5. The method of claim 4 wherein R is selected from substituted or unsubstituted $C_1$–$C_{12}$ alkyl, $C_2$–$C_{12}$ monoolefin, phenyl, cyclohexyl and 2-furyl.

6. The method of claim 5 wherein R is selected from substituted or unsubstituted $C_1$–$C_4$ alkyl, $C_2$–$C_4$ monoolefin, and the halogen substituent is chlorine.

7. The method of claim 4 wherein phosgene is added to a mixture of the aldehyde and catalyst at a temperature of from 0° to 30° C.

8. The method of claim 7 wherein the mole ratio of phosgene to aldehyde is from 1.1–1.2 to 1 and the temperature is from 0° to 30° C.

9. The method of claim 4 wherein the catalyst is selected from tetrabutyl guanidine, pentabutylguanidine, hexabutylguanidinium chloride, octabutyl biguanidinium chloride, phenyldiethyliminiumtetramethylguanidinium chloride, dimethylimidazoliniumtetrabutylguanidinium chloride, phenyltetraethylamidinium chloride, and N,N-dibutyl-N'-octylpyrrolidinium chloride.

10. The method of claim 9 wherein the catalyst is present in an amount of from 0.001 to 10 mole percent, based on the molar amount of the aldehyde reactant.

11. The method of claim 1 wherein the aldehyde is acetaldehyde, and the catalyst is pentabutylguanidine, which is present in a catalytic amount.

12. The method of claim 11 wherein phosgene is added to a mixture of acetaldehyde and pentabutylguanidine at a temperature of from 0° to 30° C., the catalyst being present in an amount of from 0.5 to 5 mole percent, based on the molar amount of the acetaldehyde.

* * * * *